(12) United States Patent
Smith

(10) Patent No.: US 6,581,454 B1
(45) Date of Patent: Jun. 24, 2003

(54) APPARATUS FOR MEASUREMENT

(75) Inventor: David Randolph Smith, Bellville, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/366,395

(22) Filed: Aug. 3, 1999

(51) Int. Cl.[7] .......................... E21B 47/01; E21B 47/10; E21B 36/00; G01D 5/26; G08C 23/06
(52) U.S. Cl. ....................... 73/152.54; 73/152.46; 73/152.28; 73/152.18; 73/863.23; 73/864.74; 73/863.81; 166/250.11; 166/236; 166/252.1; 175/50; 175/59
(58) Field of Search ..................... 73/152.54, 152.46, 73/152.28, 152.55, 152.58, 152.18, 152.19, 152.05, 863.23, 864.74, 863.81, 863.83; 166/252.1, 250.11, 228, 236, 242.3; 175/59, 60, 50

(56) References Cited

U.S. PATENT DOCUMENTS

| | | | | |
|---|---|---|---|---|
| 2,671,323 A | * | 3/1954 | Richert | 62/125 |
| 4,222,874 A | * | 9/1980 | Connelly | 210/650 |
| 4,872,507 A | * | 10/1989 | Ronco, Sr. et al. | 166/57 |
| 5,200,705 A | * | 4/1993 | Clark et al. | 324/338 |
| 5,353,873 A | * | 10/1994 | Cooke, Jr. | 166/253 |
| 5,503,014 A | * | 4/1996 | Griffith | 73/155 |
| 5,661,236 A | * | 8/1997 | Thompson | 73/152.18 |
| 5,804,713 A | * | 9/1998 | Kluth | 73/152.01 |
| 6,003,620 A | * | 12/1999 | Sharma et al. | 175/50 |
| 6,116,085 A | * | 9/2000 | Moffatt et al. | 73/152.46 |
| 6,230,557 B1 | * | 5/2001 | Ciglenec et al. | 73/152.01 |

* cited by examiner

Primary Examiner—Helen Kwok
Assistant Examiner—David J. Wiggins

(57) ABSTRACT

An apparatus is provided comprising a first tubular having an inside surface and outside surface defining an outside diameter; a second tubular concentric with the first tubular, the second tubular having an inside surface defining an inside diameter greater than the outside diameter of the first tubular, an outside surface, and a longitudinal axis; a plurality of spacers between the first and second tubulars, each spacer having a longitudinal axis parallel to the longitudinal axis of the second tubular, wherein at least one spacer is hollow; and at least one data sensing device and/or at least one data collecting device and/or at least one data transmitting device is carried within the at least one hollow spacer.

25 Claims, 2 Drawing Sheets

APPARATUS FOR MEASUREMENT

FIELD OF THE INVENTION

This invention relates to an apparatus for measurement and solid fluid filtering, particularly an apparatus for measurement during exploration and production of subsurface resources that simultaneously reduces solids from being produced while allowing fluids to be produced into a production conduit.

BACKGROUND OF THE INVENTION

Various properties are typically monitored in wells, such as flow, pressure, vibration, sound, strain, light frequency and changes thereof, electrical resistance and conductance, displacement, and temperature. Measurement devices are typically either run down on wireline tools, or in lines attached externally to the drill or production piping. Wireline tool measurement techniques allow for measurements over short periods of time, since wireline tools are typically not left in a well. Additional conduits disposed in the well outside of the production conduit reduce the overall size of the drilling or production conduits which fluids can be produced through, as space must be made to accommodate the additional instrumentation line in the wellbore.

U.S. Pat. No. 5,202,939 teaches the art of using optic fiber sensors for pressure, temperature, and strain, with the Fabry-Perot interferometer and cross-correlation methods using a Fizeau interferometer. The Fabry-Perot optic sensing crevice could be used for measuring physical parameters within wellbore if the optics could be successfully carried downhole.

SUMMARY OF THE INVENTION

There is a need for an apparatus to be disposed permanently in the wellbore which will allow full-time measurement while minimizing an reduction to flow area in the production conduit. In a first embodiment there is provided an apparatus comprising:

a first tubular having an inside surface and outside surface defining an outside diameter;

a second tubular concentric with and said first tubular, said second tubular having an inside surface defining an inside diameter greater than the outside diameter of said first tubular, an outside surface, and a longitudinal axis;

a plurality of spacers between said first and second tubulars, each said spacer having a longitudinal axis parallel to the longitudinal axis of said second tubular, wherein at least one said spacer is hollow; and at least one means for sensing data and/or at least one means for collecting, data and/or at least one means for transmitting data carried within said at least one hollow spacer.

In a second embodiment there is provided an apparatus for measurement comprising:

a cylindrical shaped membrane having a longitudinal axis, said membrane comprising at least one wire wound helically around a plane parallel to said longitudinal axis, thereby forming a cylindrical shaped membrane having an inside surface defining an inside diameter and an outside surface defining an outside diameter, wherein at least one said wire is hollow; and at least one means for sensing data and/or at least one means for collecting data and/or at least one means for transmitting data carried within said at least one hollow wire.

In another embodiment, there is provided a process for taking measurements in a well, said process comprising:

providing a wellbore;

running means for sensing data and means for collecting data and means for transmitting data within an apparatus placed in the wellbore, said apparatus comprising a first tubular having an inside surface and outside surface defining an outside diameter, a second tubular concentric with and said first tubular, said second tubular having an inside surface defining an inside diameter greater than the outside diameter of said first tubular, an outside surface, and a longitudinal axis, and a plurality of spacers between said first and second tubulars, each said spacer having a longitudinal axis parallel to the longitudinal axis of said second tubular, wherein at least one said spacer is hollow, wherein said one means for sensing data and means for collecting data and means for transmitting data are carried within said at least one hollow spacer.

sensing and collecting data depicting certain well conditions; and transmitting said data through said means for transmitting data.

DETAILED DESCRIPTION

Figure 1:
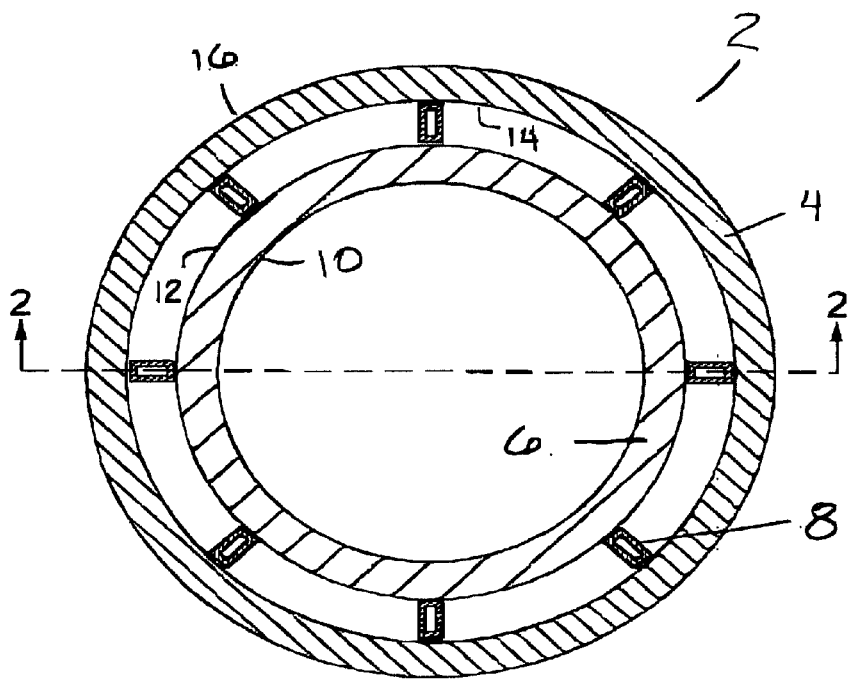
FIG. 1 shows an end view of one embodiment of the apparatus.

The apparatus of the invention provides a means for taking measurements within a wellbore by disposing in a well a permanent apparatus that allows full access through the longitudinal axis of the production conduit. The measurements may be made by using equipment, such as screens, which have been modified to carry the necessary instrumentation and provide a conduit path for data transmission through the equipment.

In a first embodiment of the invention an apparatus comprises a first tubular having an inside surface and outside surface defining an outside diameter and a second tubular concentric with the first tubular. The second tubular has an inside surface defining an inside diameter greater than the outside diameter of the first tubular, an outside surface, and a longitudinal axis. A plurality of spacers exist between the concentric first and second tubulars. Each spacer has a longitudinal axis parallel to the longitudinal axis of the second tubular and at least one of the spacers is hollow. Thus, the apparatus of the first invention could be a series of concentric tubes, such as a screen with one or more of the tube spacers modified to be a hollow spacer. At least one means for sensing data and/or at least one means for collecting data and/or at least one means for transmitting data is run through and carried within the at least one hollow spacer. The means for sensing, collecting and transmitting data may be the same means, or different means.

By "hollow spacer" is meant a spacer, typically circular or rectangular in cross-section, which has an opening running parallel to the longitudinal axis of the spacer. It is anticipated that the hollow spacer will typically take the form of a tubular, which is round or rectangular in cross-section, wherein the inside diameter forms the opening which runs parallel to the longitudinal axis.

The means for sensing data, the means for collecting data and the means for transmitting data may be any conveyance medium used for such purposes. For example, the means for sensing data may be any combination of well known measurand devices known to those familiar with the art of measurements. Examples include quartz pressure gauges, thermocouples, thermisters, microphones, accelerometers, stain gauges, optic sensors such as Fiber Braggs gratings, Fabry-Perot interferometers. The means for transmitting data may be a communication cable, electrical cable, a optic fiber, or the like. Thereby, multiple well parameters can be measured, such as temperature, pressure, or flow rate. Or information from downhole devices, such as pumps or other equipment, may be transmitted up the data transmission device.

The apparatus would be effective in making use of Fabry-Perot interferometer cavity optic sensor devices. For example, if such interferometer cavity optic sensor devices were disposed in subterranean wells, pressure due to the cavity distance change could be measured by various parameters such as pressure, strain, and temperature.

Combinations of data sensing/collecting/transmitting means may be carried in a single apparatus, either by running more than one means down a single hollow spacer, or by utilizing more than one hollow spacer. Or the means themselves may be a single device which can sense, collect and transmit data.

The apparatus may be further modified, and greater instrumentation may be achieved, by changing the structure of either the inner or outer tubular. For example, the inside surface and the outside surface of the second tubular may define a wall wherein the wall comprises at least one hollow wire wound helically around a plane parallel to the longitudinal axis. At least one means for sensing data and/or at least one means of collecting data and/or at least one means of transmitting data may also be run through and carried within the hollow wire wall.

In another embodiment of the invention an apparatus for measurement comprises a cylindrical shaped membrane having a longitudinal axis. The membrane comprises at least one wire wound helically around a plane parallel to said longitudinal axis, thereby forming a cylindrical shaped membrane having an inside surface. As described hereinabove, at least one of the wires is hollow. At least one means for sensing data and/or at least one means for collecting data and/or at least one means for transmitting data is thus run through and carried within the at least one hollow wire.

A second cylindrical membrane, concentric with the first membrane, may be added to the second embodiment, substantially as already herein described. Spacers, at least one of which may be hollow, may be placed between the cylindrical membranes, allowing still more instrumentation to be carried within the device.

There is also provided a method for taking measurements within a well using the apparatus described. The process comprises providing a wellbore, placing an apparatus, as already herein described, within the wellbore, and running means for sensing data, and collecting data and transmitting data within the apparatus. The data depicting certain well conditions are sensed, collected and transmitted through the apparatus.

The apparatus as described maintains the size of the production conduit of the well while allowing real time measurements to take place. Further, the apparatus allows for multiple functions to be simultaneously performed downhole. For example, when the apparatus is a modified screen, as data is sensed, collected and transmitted, the screen can filter solid flow from fluid flow while allowing fluid flow into a production conduit.

Figure 2:
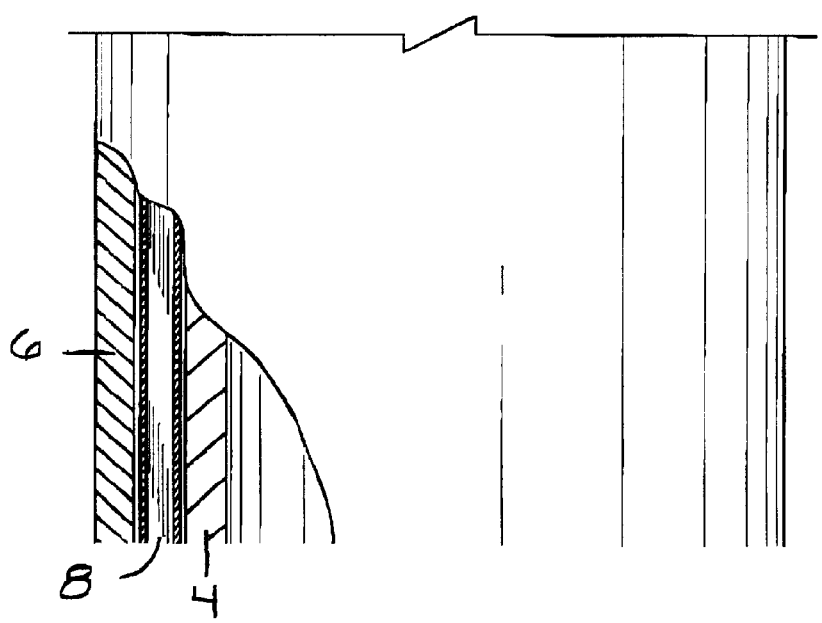
FIG. 2 is a sectional view of FIG. 1.

Referring to FIG. 1 and FIG. 2, the apparatus 2 consists of an inner tubular 4 and a concentric outer tubular 6 which are spaced apart by one or more spacers 8. At least one of the one or more spacers 8 are hollow, to allow instrumentation to be carried downhole with the apparatus.

The inner tubular 4 has an inside surface 10 and an outside surface 12 which defines an outside diameter. The outer tubular 6 has an inside surface 14 which defines an inside diameter greater than the outside diameter of the first tubular, an outside surface 16, and a longitudinal axis. The spacers 8 exist between the concentric inner and outer tubulars. Each spacer has a longitudinal axis parallel to the longitudinal axes of the tubulars. The spacers are attached to the outside surface 12 of the inner tubular 4 and the inside surface 14 of the outer tubular 6. A typical method of attached is via spot welding.

Figure 3:
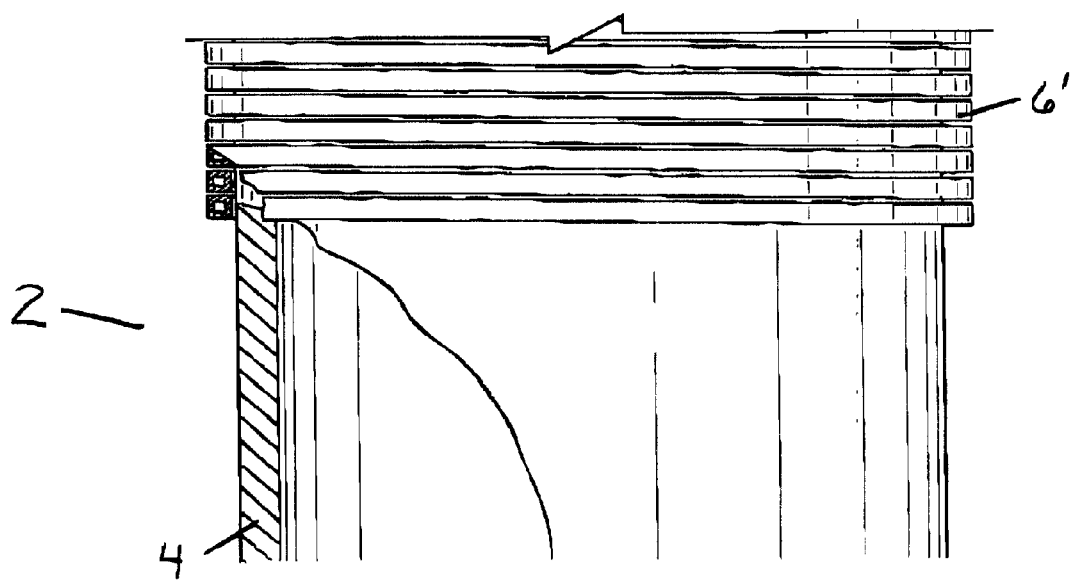
FIG. 3 is a sectional view of a second embodiment of the apparatus.

FIG. 3 shows a second embodiment of the invention where the outer tubular 6' is formed from a wire helically wrapped around the inner tubular 4. The wire is hollow to allow instrumentation to be carried downhole with the apparatus. Spacers (not shown) exist between the inner and outer tubulars, as already herein described.

Other embodiments of the invention will be apparent to those skilled in the art from a consideration of this specification or from practice of the invention disclosed. It is intended that the specification be considered as exemplary only, with the true scope and spirit of the invention being indicated by the following claims.

I claim:

1. An apparatus comprising:
    a first tubular having an inside surface and outside surface defining an outside diameter;
    a second tubular concentric with said first tubular, said second tubular having an inside surface defining an inside diameter greater than the outside diameter of said first tubular, an outside surface, and a longitudinal axis;
    a plurality of spacers between said first and second tubulars, each said spacer having a longitudinal axis parallel to the longitudinal axis of said second tubular, wherein at least one said spacer is hollow; and
    at least one means for sensing data and/or at least one means for collecting data and/or at least one means for transmitting data carried within said at least one hollow spacer;
    wherein said means for sensing data is a Fabry-Perot interferometer cavity optic sensor device.

2. An apparatus according to claim 1 wherein said means for sensing data, said means for collecting data and said means for transmitting data are the same means.

3. An apparatus according to claim 1 wherein said inside surface and said outside surface of said second tubular define a wall; and wherein said wall comprises at least one hollow wire wound helically around a plane parallel to said longitudinal axis, and at least one means for sensing data and/or at least one means for collecting data and/or at least means for transmitting data carried within said at least one hollow wire.

4. An apparatus according to claim 3 wherein said means for transmitting data carried within said hollow wire is selected from a communication cable, an electrical cable, an optic fiber cable, and combinations thereof.

5. An apparatus according to claim 3 wherein said means for sensing data is a Fabry-Perot interferometer cavity optic sensor device.

6. An apparatus according to claim 3 wherein said means for sensing data, said means for collecting data and said means for transmitting data carried within said hollow wire are the same means.

7. An apparatus for measurement comprising:
a cylindrical shaped membrane having a longitudinal axis, said membrane comprising at least one wire wound helically around a plane parallel to said longitudinal axis, thereby forming a cylindrical shaped membrane having an inside surface defining an inside diameter and an outside surface defining an outside diameter, wherein at least one said wire is hollow; and
at least one means for sensing data and/or at least one means for collecting data and/or at least one means for transmitting data carried within said at least one hollow wire;
wherein said means for sensing data is a Fabry-Perot interferometer cavity optic sensor device.

8. An apparatus according to claim 7 wherein said means for transmitting data is selected from a communication cable, an electrical cable, an optic fiber cable, and combinations thereof.

9. An apparatus according to claim 7 wherein said means for sensing data, said means for collecting data and said means for transmitting data are the same means.

10. An apparatus according to claim 7 further comprising a second cylindrical shaped membrane concentric with said first membrane, said second membrane having an outside surface defining an outside diameter smaller than the inside diameter of said first membrane; and at least one spacer between said first and second membranes, said at least one spacer having a longitudinal axis parallel to the longitudinal axis of said first membrane.

11. An apparatus according to claim 10 wherein said at least one said spacer is hollow; said apparatus further comprising at least one means for sensing data and/or at least one means for collecting data and/or at least one means for transmitting data carried within said at least one hollow spacer.

12. An apparatus according to claim 11 wherein said means for transmitting data carried within said hollow spacer is selected from a communication cable, an electrical cable, an optic fiber cable, and combinations thereof.

13. An apparatus according to claim 11 wherein said means for sensing data, said means for collecting data and said means for transmitting data carried within said hollow wire are the same means.

14. A process for taking measurements in a well according to claim 15 wherein said means for transmitting data is selected from a communication cable, an electrical cable, an optic fiber cable, and combinations thereof.

15. A process for taking measurements in a well for taking measurements in a well, said process comprising:
providing a wellbore;
running means for sensing data and means for collecting data and means for transmitting data within an apparatus placed in the wellbore, said apparatus comprising a first tubular having an inside surface and outside surface defining an outside diameter, a second tubular concentric with and said first tubular, said second tubular having an inside surface defining an inside diameter greater than the outside diameter of said first tubular, an outside surface, and a longitudinal axis, and a plurality of spacers between said first and second tubulars, each said spacer having a longitudinal axis parallel to the longitudinal axis of said second tubular, wherein at least one said spacer is hollow, wherein said one means for sensing data and means for collecting data and means for transmitting data are carried within said at least one hollow spacer;
sensing and collecting data depicting certain well conditions; and
transmitting said data through said means for transmitting data;
wherein said means for sensing data is a Fabry-Perot interferometer cavity optic sensor device.

16. A process for taking measurements in a well according to claim 15 wherein said means for sensing data, said means for collecting data and said means for transmitting data are the same means.

17. A process for taking measurements in a well according to claim 15 wherein said inside surface and said outside surface of said second tubular define a wall; and wherein said wall comprises at least one hollow wire wound helically around a plane parallel to said longitudinal axis, and at least one means for sensing data and/or at least one means for collecting data and/or at least means for transmitting data are carried within said at least one hollow wire.

18. A process for taking measurements in a well according to claim 17 wherein said means for transmitting data carried within said hollow wire is selected from a communication cable, an electrical cable, an optic fiber cable, and combinations thereof.

19. A process for taking measurements in a well according to claim 17 wherein said means for sensing data, said means for collecting data and said means for transmitting data carried within said hollow wire are the same means.

20. A process for taking measurements in a well according to claim 15 wherein said apparatus is a screen having a characteristic of filtering solid flow from fluid flow while allowing fluid flow into a production conduit of said well; said process further comprising producing fluid through said production conduit simultaneously with said data sensing, collection and transmission.

21. A screen for use within a wellbore, comprising:
a first tubular having an inside surface and outside surface defining an outside diameter;
a second tubular concentric with and said first tubular, said second tubular having an inside surface defining an inside diameter greater than the outside diameter of said first tubular, an outside surface, and a longitudinal axis;
a plurality of spacers between said first and second tubulars, each said spacer having a longitudinal axis substantially equal to and parallel to the longitudinal axis of said second tubular, wherein at least one said spacer is hollow; and
at least one means for sensing data and/or at least one means for collecting data and/or at least one means for transmitting data carried within said at least one hollow spacer.

22. A screen according to claim 21 wherein said means for transmitting data is selected from a communication cable, an electrical cable, an optic fiber cable, and combinations thereof.

23. A screen according to claim 21 wherein said means for sensing data is selected from a fiber optic, a temperature sensing device, a pressure sensing device, a flow sensing device, a vibration sensing device, an electrical sensing device, an acoustic sensing device, a resistance sensing device, a strain sensing device, an interferometer, an optic sensing device, and combinations thereof.

24. A screen according to claim 23, wherein said means for sensing data is a Fabry-Perot interferometer cavity optic sensor device.

25. A screen according to claim 21 wherein said means for sensing data, said means for collecting data and said means for transmitting data are the same means.

* * * * *